United States Patent [19]

Rinaldi et al.

[11] Patent Number: 5,891,470
[45] Date of Patent: Apr. 6, 1999

[54] SOFTGEL FORMULATION CONTAINING RETINOL

[75] Inventors: Marie A. Rinaldi, St. Petersburg, Fla.; Subhash J. Saxena, Belmont, Calif.; Paul C. Tutschek, Largo, Fla.

[73] Assignees: Advanced Polymer Systems, Inc., Redwood City, Calif.; R.P. Scherer Corporation, Troy, Mich.

[21] Appl. No.: 62,138

[22] Filed: Apr. 17, 1998

[51] Int. Cl.$^6$ .................. A61K 9/48; A61K 9/52; A61K 9/54; A61K 9/58
[52] U.S. Cl. ............ 424/451; 424/452; 424/455; 424/456; 424/457; 424/458; 424/462; 427/213.35; 514/963; 514/965
[58] Field of Search ............ 424/451, 452, 424/455, 456, 457, 458, 462; 427/213.35; 514/951, 962, 963, 964, 965

[56] References Cited

U.S. PATENT DOCUMENTS

| | | | |
|---|---|---|---|
| 4,369,180 | 1/1983 | Mihalovits | 424/177 |
| 4,690,825 | 9/1987 | Won | 424/501 |
| 4,826,828 | 5/1989 | Wilmott et al. | 514/63 |
| 4,873,091 | 10/1989 | Jankower et al. | 424/489 |
| 4,888,363 | 12/1989 | Dulak et al. | 514/725 |
| 5,055,300 | 10/1991 | Gupta | 424/409 |
| 5,073,365 | 12/1991 | Katz et al. | 424/489 |
| 5,082,661 | 1/1992 | Melnik et al. | 424/401 |
| 5,135,740 | 8/1992 | Katz et al. | 424/401 |
| 5,145,675 | 9/1992 | Won | 424/78.31 |
| 5,516,793 | 5/1996 | Duffy | 514/474 |
| 5,559,149 | 9/1996 | Clum et al. | 514/529 |
| 5,587,149 | 12/1996 | Punto et al. | 424/59 |

FOREIGN PATENT DOCUMENTS

| | | |
|---|---|---|
| 0 440 398 | 8/1991 | European Pat. Off. . |
| 0 586 106 | 3/1994 | European Pat. Off. . |
| 0 781 551 | 7/1997 | European Pat. Off. . |
| 93/00085 | 1/1993 | WIPO . |

*Primary Examiner*—Nathan M. Nutter
*Attorney, Agent, or Firm*—Heller Ehrman White & McAuliffe

[57] ABSTRACT

A softgel formulation containing retinol comprises a soft gelatin shell and a fill material within that shell containing retinol-impregnated microparticles. The fill material may be an optionally thickened silicone oil, or may be an emulsion comprising a silicone oil. Ascorbic acid may be present as ascorbic acid-impregnated microparticles and/or within the emulsion.

35 Claims, No Drawings

SOFTGEL FORMULATION CONTAINING RETINOL

BACKGROUND OF THE INVENTION

This invention relates to a softgel formulation containing retinol, and to a softgel formulation containing both retinol and ascorbic acid.

Retinol, along with other retinoids, has enjoyed increasing popularity as an active ingredient in skin care compositions, especially for acne, photoaging, and sun damage. However, more so than other retinoids, retinol tends to decompose on exposure to light, heat, and oxygen. The problem of decomposition has been addressed to some extent by formulating retinol with antioxidants and chelating agents, and storing it in opaque or colored containers, and several patents and published applications, for example, PCT International Application Publication No. WO 93/00085 and European Patent Application Publication Nos. 0 440 398 and 0 596 106, all to Johnson & Johnson, describe water-in-oil emulsions containing retinol, which are asserted to be stable. European Patent Application Publication No. 0 781 551, to Advanced Polymer Systems, discloses an oil-in-water emulsion containing retinol, in which the retinol is entrapped within the pores of solid porous polymeric microparticles. The disclosures of these and other documents referred to in this application are incorporated herein by reference.

Softgel (soft gelatin capsule) formulations have recently become of greater interest in the formulation of products for topical application to the skin, because the softgels provide an attractive single use method for dispensing the product. Typically, these softgels contain 0.1 mL to 2 mL of a fill material, and have a "twist-off" or other removable feature at one end for dispensing the fill material. Such softgels can be prepared by methods well known for the preparation of softgels for oral dosage formulations, i.e. by encapsulating the fill material between two sheets of gelatin as it passes between a pair of die rolls having surface cavities shaped to form the desired shape of the resulting softgel.

However, it is well known in the art that unmodified softgels are incompatible with water, and that typical emulsions, whether water-in-oil or oil-in-water, will degrade the gelatin shell of a softgel.

U.S. Pat. No. 5,587,149 (Punto et al.) discloses a softgel formulation for water-soluble active ingredients, such as ascorbic acid (vitamin C), where the fill material comprises an emulsion of which a first phase includes polyethylene glycol (into which the water-soluble active ingredient is dissolved) and the second phase includes a silicone fluid.

It would be of value to have a softgel formulation containing retinol, and a formulation containing retinol and ascorbic acid.

BRIEF SUMMARY OF THE INVENTION

In a first aspect, this invention provides a softgel formulation containing retinol and optionally containing ascorbic acid, comprising:
(a) a soft gelatin shell; and
(b) a fill material within the shell, the fill material comprising:
  (i) an optionally thickened silicone oil,
  (ii) retinol-impregnated microparticles, and optionally
  (iii) ascorbic acid-impregnated microparticles.
In a second aspect, this invention provides a softgel formulation containing retinol and optionally containing ascorbic acid, comprising:
(a) a soft gelatin shell; and
(b) a fill material within the shell, the fill material comprising:
  (i) an emulsion comprising a polyethylene glycol and a silicone oil and optionally from 0.01% to 10% by weight of the fill material of ascorbic acid, and
  (ii) retinol-impregnated microparticles, and optionally
  (iii) ascorbic acid-impregnated microparticles.

DETAILED DESCRIPTION OF THE INVENTION

According to the first aspect of this invention, there are obtained softgel formulations for retinol and for retinol and ascorbic acid, in which the retinol and the ascorbic acid, if present, are present in the fill material for the softgel capsule impregnated into porous microparticles. According to the second aspect of this invention, there are obtained softgel formulations for retinol and for retinol and ascorbic acid, in which the retinol is present in the fill material for the softgel capsule impregnated into porous microparticles and the ascorbic acid, if present, is present in the fill material either in free form and/or impregnated into porous microparticles. Formulations according to this invention are stable and topically cosmetically acceptable, and are also stable in softgels, thereby providing attractive topical forms for retinol, and for retinol and ascorbic acid, in convenient single-use containers.

Number ranges given in the specification, such as size ranges and the like, should be considered approximate, unless specifically stated.

Ingredient names are taken from the *International Cosmetic Ingredient Handbook*, 3rd edition, 1995.

The microparticles

Suitable microparticles for this invention are solid, water-insoluble, polymeric microparticles having a network of interconnected pores open to the particle surface, providing substantially full communication between the internal pore space and the particle exterior surface. Microparticles of this type, and methods for their preparation, are disclosed in U.S. Pat. Nos. 4,690,825 (Won), 4,873,091 (Jankower et al.), 5,073,365 (Katz et al.), 5,135,740 (Katz et al.), and 5,145,675 (Won).

The porous microparticles are generally spherical in shape and have a weight average diameter from less than 1 $\mu$m to 500 $\mu$m or more, particularly from 5 $\mu$m to 100 $\mu$m, more particularly from 10 $\mu$m to 50 $\mu$m, especially about 20 $\mu$m. The pore dimensions within the microparticles may vary, with optimum dimensions depending on the polymers used to form the microparticles and the diffusive characteristics of the material to be impregnated. Typical pore volumes are from 0.01 cm$^3$/g to 4 cm$^3$/g, particularly from 0.1 cm$^3$/g to 2 cm$^3$/g; typical surface areas are from 1 m$^2$/g to 500 m$^2$/g, particularly from 20 m$^2$/g to 350 m$^2$/g; and typical pore diameters are from 0.0001 $\mu$m to 3 $\mu$m, particularly from 0.003 $\mu$m to 1 $\mu$m. The average diameter of the microparticles may be determined by sedimentation or by a laser microsizer; the pore volume may be determined by mercury intrusion; and the surface area may be determined by nitrogen adsorption (the BET method).

The porous microparticles are composed of organic polymers and are formed by suspension polymerization of a mixture of monoethylenically unsaturated and polethylenically unsaturated monomers in the presence of a porogen (a pore-forming agent), as described in the patents listed above. Monoethylenically unsaturated monomers suitable for forming microparticles for use in this invention include styrene, ethylvinylbenzene, vinyltoluene, acrylic acid and its esters, such as ethyl acrylate, methacrylic acid and its esters, such as methyl methacrylate and lauryl methacrylate, vinyl esters, such as vinyl acetate, vinyl propionate, vinyl stearate, and vinyl laurate, vinylic ketones, such as vinyl methyl ketone and methyl isopropenyl ketone, and vinyl ethers, such as vinyl methyl ether, and the like. Polyethylenically unsaturated monomers suitable for forming microparticles for use in this invention include divinylbenzene, divinyl ketone, divinyl sulfone, polyvinyl or polyallyl esters of dibasic or polybasic acids, such as divinyl sebacate, diallyl adipate, diallyl phthalate, diallyl sebacate, polyvinyl or polyallyl ethers of diols or polyols, such as ethylene glycol divinyl ether and diethylene glycol diallyl ether, polyacrylate or polymethacrylate esters of diols or polyols, such as ethylene glycol dimethacrylate, polyethylene glycol diacrylate, trimethylolpropane trimethacrylate, and the like. Typically the monoethylenically unsaturated monomer will be present at from 20% to 80% of the monomer mixture, with the polyethylenically unsaturated monomer forming the remainder of the mixture. Preferred monomer mixtures include styrene/divinylbenzene, vinyl stearate/divinylbenzene, methyl methacrylate/ethylene glycol dimethacrylate, and lauryl methacrylate/ethylene glycol dimethacrylate.

The mixture of monomers, together with the porogen, which is typically a moderately low-boiling hydrocarbon such as heptane or toluene, and a polymerization catalyst, such as a peroxide, are added to an aqueous phase, typically containing a dispersant, and stirred to form a suspension of the organic phase in the aqueous phase with droplets of the desired size of the resulting particles. On heating and continued stirring, the monomers polymerize to form solid porous microparticles having the pores filled with the porogen. The microparticles are filtered, washed with water to remove the dispersants and then with volatile organic solvents such as isopropanol to remove unreacted monomers and the porogen, and then dried under vacuum to afford the porous microparticles.

Microparticles of this type are commercially available from Advanced Polymer Systems, Inc. under the trademark Microsponge®.

The retinol-impregnated microparticles

Retinol-impregnated microparticles suitable for use in this invention may be prepared by mixing the microparticles with a solution containing retinol and subsequently removing the solvent. Typically, the retinol-impregnated microparticles will have a retinol content from 1% to 50%, particularly from 10% to 30%, especially around 20% by weight of the impregnated microparticles; and usually contain an overage of retinol (up to 20%) to ensure adequate potency after storage.

The retinol is preferably impregnated into the microparticles as a retinoid composition containing additional ingredients, such as antioxidants and chelating agents. Typically, the retinoid composition will comprise from 5% to 95% by weight of retinol, more typically, from 10% to 70% by weight of retinol. Frequently, the retinol will be a commercial retinol blend, containing an antioxidant, such as butylated hydroxytoluene, and a dispersant, such as polysorbate 20, in addition to the retinol; and additional ingredients will be added to that retinol blend.

Typical optional additional ingredients in the retinoid composition include antioxidants. Both water-soluble and oil-soluble antioxidants may be used. Examples of water-soluble antioxidants include ascorbic acid and its salts, such as sodium ascorbate, isoascorbic acid and its salts, sodium sulfite, sodium metabisulfite, sodium thiosulfite, thiols such as thioglycerol, thiosorbitol, thiourea, thioglycolic acid, and cysteine, and the like. Examples of oil-soluble antioxidants include BHT (butylated hydroxytoluene), BHA (butylated hydroxyanisole), tocopherol (vitamin E), tocopheryl acetate, ascorbyl palmitate, hydroquinone, di-t-butylhydroquinone, propyl gallate, and the like. The amount of antioxidant may vary, and is not critical to this invention provided that sufficient is present to give the retinol the desired stability. In most applications, an amount ranging from 0.01% to 10% by weight of the retinoid composition will be appropriate.

Other optional ingredients in the retinoid composition include chelating agents such as EDTA (ethylenediaminetetraacetic acid) and its salts, for example disodium EDTA, trisodium NTA, etidronic acid and its salts, sodium dihydroxyethylglycinate, citric acid and its salts, and the like. The amount of chelating agent may likewise vary and is not critical to this invention; and in most applications, an amount ranging from 0.01% to 1% by weight of the retinoid composition is sufficient.

Typically, the retinol (retinol blend) and any additional ingredients will be dissolved in a volatile organic solvent, such as a lower alcohol or lower ketone, for example isopropanol or acetone, and the solution mixed with the microparticles so that the solution is absorbed into the pores of the microparticles. Once the microparticles have absorbed the solution, the solvent is removed by evaporation, typically under reduced pressure and optionally with mild heating, avoiding excessive temperatures that may speed decomposition or oxidation of the retinol.

Because of the sensitivity of retinol to light, especially ultraviolet light, heat, and oxygen, the retinol and all compositions containing it will typically be handled under yellow light, and in opaque or colored containers, and an oxygen-free atmosphere, e.g. under nitrogen or other inert gas. Solvents will typically be degassed and/or purged with nitrogen before use, fill materials and intermediate compositions degassed, and storage containers purged with nitrogen both before and after filling with a retinol-containing composition, such as the retinol-impregnated microspheres and fill materials containing retinol. The ascorbic acid-impregnated microparticles The ascorbic acid-impregnated microparticles may be prepared in the same manner as described above for the retinol-impregnated microspheres, except for those differences occasioned by the relatively greater stability of the ascorbic acid and its water solubility. Accordingly, typically the ascorbic acid and any optional additional ingredients such as antioxidants and chelating agents are dissolved in water, optionally containing a lower alcohol, and the microparticles mixed with the resulting solution so that it is absorbed into the pores of the microparticles. The solvent is then removed under reduced pressure. Typically, the ascorbic acid-impregnated microparticles will have an ascorbic acid content from 10% to 70%, particularly from 30% to 60%, especially around 50% by weight of the impregnated microparticles.

The silicone oils

The term "silicone oil" is used here with its usual meaning of a liquid siloxane-containing polymer. Suitable silicone oils for use in this invention are polyalkyl siloxanes and polyalkyl phenyl siloxanes, having dynamic viscosities between less than 1 to as great as $10^7$ centistokes at 25° C. Suitable low viscosity silicone oils are the cyclic polymers of dimethylsiloxane containing from three to six (typically four or five) siloxane units in the ring, commonly referred to as cyclomethicone. Various cyclomethicones are available, having different proportions of the trimer, tetramer, pentamer, and hexamer components. Other suitable low viscosity silicone oils include the lower polydimethylsiloxanes (dimethicones), such as hexamethyldisiloxane, and lower polyalkylphenylsiloxanes, such as phenyldimethicones. Other suitable silicone oils include dimethiconol, dimethicone copolyol, laurylmethicone, laurylmethicone copolyol, cetyl dimethicone copolyol, and the like. Examples include Dow Corning 200 (dimethicone, available in various viscosities), 244, 245, 344, and 345 (cyclomethicone), Q2-5200 (lauryl dimethicone copolyol), 3225C (cyclomethicone and dimethicone copolyol), 1401 (cyclomethicone and dimethiconol), 1403 (dimethicone and dimethiconol), and Abil WE09 (polyglycerol-4 isostearate/cetyl dimethicone copolyol/hexyl laurate).

Optionally, and desirably when it is not a part of an emulsion, the silicone oil used in this invention is thickened, or gelled, to increase its viscosity. Suitable thickening agents include fumed silica and other anhydrous thickening agents, and preferred thickening agents, especially when the silicone oil is not part of an emulsion, are the high viscosity polysiloxanes such as high molecular weight dimethicones and phenyldimethicones. Suitable thickening agents are Dow Corning SE-30, a gum-like high molecular weight dimethicone having a viscosity between $10^5$ and $4 \times 10^6$ centipoise, and General Electric Vicasil, another high molecular weight dimethicone. Typically, the amount of thickening agent present in the silicone oil will be from about 0.5% to 40%, more typically around 10%, by weight of the total silicone oil content.

Mixtures of high and low viscosity dimethicones may also be used, such as Dow Coming X2-1146A.

A preferred silicone oil is a thickened cyclomethicone composition, such as cyclomethicone thickened with a high molecular weight dimethicone or polysilicone-11, or a cyclomethicone and dimethicone cross-polymer, such as Dow Corning 2-940 silicone gel.

Especially when the silicone oil is present in an emulsion, as in the third and fourth aspects of this invention, it may be accompanied by a low molecular weight hydrocarbon oil, for example having from 12 to 30 carbon atoms, such as mineral oil and isoparaffin, or a vegetable oil, or mixture thereof.

The silicone oil formulations

In the silicone oil formulations of the first aspect of the invention, typically the fill material for the softgel capsules will contain one or more silicone oils, optionally thickened as described above, and retinol-impregnated microparticles, and optionally ascorbic acid-impregnated microparticles. Typically, the resulting fill material will have a retinol content of at least 0.005%, particularly at least 0.01%, more particularly at least 0.02%; and less than 5%, particularly less than 2%, more particularly less than 1%, by weight of the fill material. The ascorbic acid content, if ascorbic acid is present, will typically be at least 0.01%, particularly at least 0.1%, more particularly at least 0.3%; and less than 10%, particularly less than 5%, more particularly less than 3%, by weight of the fill material.

The fill material may also contain additional ingredients such as antioxidants, chelating agents, colorants, fragrances, preservatives, and the like, as necessary or desired, typically in amounts less than 1% by weight of the fill material; and may also contain esters, oils, and solubilizers, typically in amounts less than 10% by weight of the fill material.. Suitable antioxidants and chelating agents are those previously mentioned with regard to the retinol-impregnated microparticles previously; and suitable preservatives include the parabens, such as methylparaben, propylparaben, isopropylparaben, butylparaben, and isobutylparaben, and their salts such as sodium butylparaben, benzoic acid and its salts and esters, benzyl alcohol, urea derivatives such as diazofidinyl urea, imidazolidinyl urea, and DMDM hydantoin, sorbic acid and its salts, and the like. Suitable colorants and fragrances will be a matter of choice, provided only that they should be compatible with the fill material and the gelatin of the softgel capsule.

The fill material is typically prepared by blending the low viscosity silicone oil component(s) and the retinol-impregnated microparticles (and the ascorbic acid-impregnated microparticles, if present) and optional additional ingredients to uniformity, then mixing with the high viscosity silicone oil component(s), again mixing to uniformity, adding any volatile components such as fragrances, degassing, and finally filling the resulting fill material into softgel capsules. The filling may be accomplished by methods well known to the art; typically using a rotary die fed from two plasticized gelatin sheets which form a sealed chamber around the material being encapsulated. The size of the softgels may range from 0.5 cm to 5 cm in length, particularly 1 cm to 3 cm; and the resulting capsule volume may be from 0.1 g to 5 g, particularly from 0.3 g to 2 g, especially about 1 g. Desirably, the softgel is formed to have a "twist-off" or otherwise removable feature, such as a "neck" that may easily be cut, at one end, so that the fill material may easily and conveniently be dispensed from the softgel onto the skin. The emulsion formulations In the emulsion formulations of the second aspect of the invention, typically the fill material for the softgel capsules will contain an emulsion having a first phase containing a polyethylene glycol and a second phase containing one or more silicone oils, the emulsion also containing retinol-impregnated microparticles, and optionally ascorbic acid-either dissolved or suspended in the first phase of the emulsion ("free" ascorbic acid) and/or present in ascorbic acid-impregnated microparticles. Typically, the resulting fill material will have a retinol content of at least 0.005%, particularly at least 0.01%, more particularly at least 0.02%; and less than 5%, particularly less than 2%, more particularly less than 1%, by weight of the fill material. The ascorbic acid content, if ascorbic acid is present, will typically be at least 0.01%, particularly at least 0.1%, more particularly at least 0.3%; and less than 10%, particularly less than 5%, more particularly less than 3%, by weight of the fill material, present either in the emulsion and/or in ascorbic acid-impregnated microparticles. It is a particular advantage of the emulsion formulation of this invention that the emulsion may contain free ascorbic acid in the first phase of the emulsion; so that if ascorbic acid is present in the formulation, at least a part of it is typically present as "free" ascorbic acid. The fill material may also contain additional ingredients such as antioxidants, chelating agents, colorants, fragrances, preservatives, and the like, as necessary or desired, typically in amounts less than 1% by weight of the fill material, present in either or both of the first and second emulsion phases; and each of the phases may also contain a thickening agent suitable for that phase.

The first emulsion phase includes one or more low molecular weight polyethylene glycols, having from 4 to 150, preferably 8 to 20, ethylene oxide units per molecule on average, such as PEG-8, PEG-20, or a mixture thereof, and it is this phase into which the "free" ascorbic acid, i.e. the ascorbic acid which is not found in the ascorbic acid-impregnated microparticles, is dissolved. This first phase may include glycerin, and may also include water up to about 10% by weight of the emulsion. However, because water is generally deleterious to the integrity of softgel capsules because of the solubility of gelatin in water, especially at elevated temperatures, the use of substantial amounts of water in the emulsions of this invention must be closely monitored. The amount of water, if present, is typically no more than 5% by weight of the emulsion. The polyethylene glycols of the first phase may be present in from 20% to 80%, preferably 20% to 50% by weight of the emulsion.

The second emulsion phase comprises a silicone oil, of the type described previously, and may optionally contain low molecular weight hydrocarbon oils and/or vegetable oils, also as described previously. The silicone oil typically comprises from 10% to 50%, preferably 20% to 40% by weight of the emulsion.

The emulsion will also contain a dispersant, typically a polysorbate such as polysorbate 20 or polysorbate 80, to stabilize the emulsion.

The emulsion may be prepared by methods well known to the art, typically by mixing the first (polyethylene glycol) phase ingredients and the dispersant with heating until a uniform solution or dispersion is obtained (optionally in several stages, as discussed further in Examples 3 and 4), mixing the second (silicone oil) phase ingredients with heating until a uniform solution or dispersion is obtained ( optionally in several stages), then adding the first phase to the second phase with agitation to form an emulsion of the first phase in the second phase. These and all other processing steps are typically performed under an inert atmosphere, for example of nitrogen, and all steps involving retinol are performed under yellow light to protect the retinol from exposure to ultraviolet light. The emulsion is cooled with stirring. Once the emulsion is sufficiently cooled, it is homogenized; and the retinol- and ascorbic acid-impregnated microparticles, and temperature-sensitive or volatile ingredients, such as the fragrance, are added and uniformly dispersed in the emulsion to form the fill material for the softgel capsules. The emulsion formulations may be degassed in the same manner as the silicone oil formulations. The softgel capsules are filled with the emulsion in the manner described previously.

The invention is illustrated by the following Preparations and Examples.

PREPARATION 1
Retinol-impregnated Microparticles, 22.5%
Retinol-impregnated microparticles were prepared to the following formulation:

| Ingredient | Weight percent |
| --- | --- |
| Retinol blend[1] | 50.000 |
| Microparticles[2] | 48.931 |
| Tocopheryl acetate | 1.000 |
| Ascorbic acid | 0.023 |
| Disodium EDTA | 0.023 |
| Propyl gallate | 0.023 |

[1]The retinol blend contained approximately 45.0% retinol, 51.25% polysorbate 20, 3.0% BHT, and 0.75% BHA.
[2]The microparticles used were Microsponge ® (Advanced Polymer Systems, Inc.), porous methyl methacrylate/ethylene glycol dimethacrylate microparticles, having a weight average particle diameter of 20 $\mu$m, a surface area of 225 m$^2$g, and a pore volume of 1 cm$^3$/g.

Under yellow light, the retinol blend, tocopheryl acetate, ascorbic acid, disodium EDTA, and propyl gallate were dissolved in isopropanol, using 50 g isopropanol per 50 g of retinol blend. The resulting solution was purged with nitrogen, and was mixed with the microparticles, agitating until the solution was absorbed. Once the solution had been fully absorbed by the microparticles, the solvent was removed under vacuum, and the impregnated microparticles were stored in brown glass jars under a nitrogen atmosphere.

PREPARATION 2
Ascorbic Acid-impregnated Microparticles, 50%
Ascorbic acid-impregnated microparticles were prepared to the following formulation:

| Ingredient | Weight percent |
| --- | --- |
| Ascorbic acid | 50.00 |
| Microparticles[1] | 49.40 |
| Citric acid, anhydrous | 0.20 |
| Disodium EDTA | 0.20 |
| Propyl gallate | 0.10 |
| Sodium metabisulfite | 0.10 |

[1]The microparticles used were Microsponge ® (Advanced Polymer Systems, Inc.), porous methyl methacrylate/ethylene glycol dimethacrylate microparticles, having a weight average particle diameter of 20 $\mu$m, a surface area of 225 m$^2$/g, and a pore volume of 1 cm$^3$/g.

The ascorbic acid, citric acid, disodium EDTA, propyl gallate, and sodium metabisulfite were dissolved in water, using 83.3 g water per 50 g ascorbic acid; and the microparticles were added to the resulting solution. When the solution had been completely absorbed by the microparticles, the water was removed by drying the microparticles under vacuum.

EXAMPLE 1
Softgel Containing Retinol, 0.3%, in Silicone
A fill material for softgel capsules was prepared from the following formulation:

| Ingredient | Weight percent |
| --- | --- |
| Cyclomethicone and polysilicone-11 (Gransil RPS gel) | 58.0 |
| Cyclomethicone (Dow Corning 245 fluid) | 40.3 |
| Retinol-impregnated microparticles [Preparation 1] | 1.6 |
| Fragrance | 0.1 |

The process was carried out under nitrogen and yellow light. The retinol-impregnated microparticles were dispersed in the cyclomethicone and mixed to uniformity; and the resulting mixture added to the cyclomethicone and polysilicone-11 and mixed to uniformity. The fragrance was then added and also mixed to uniformity. The resulting fill material was degassed under vacuum, and filled into 6 minim twist-off softgel capsules, each containing 0.32 g fill material, to give a product containing 0.30% (with a 20% overage) retinol by weight of the fill material.

EXAMPLE 2
Softgel Containing Retinol, 0.3%, in Silicone
A fill material for softgel capsules was prepared from the following formulation:

| Ingredient | Weight percent |
| --- | --- |
| Cyclomethicone and polysilicone-11 (Gransil RPS gel) | 58.0 |
| Cyclomethicone (Dow Corning 245 fluid) | 35.2 |
| $C_{12-15}$ Alkyl benzoate (Finsolv TN) | 5.0 |
| Retinol-impregnated microparticles [Preparation 1] | 1.6 |
| BHT | 0.1 |
| Fragrance | 0.1 |

The process was carried out under nitrogen and yellow light. The retinol-impregnated microparticles, $C_{12-15}$ alkyl benzoate, and BHT were dispersed in the cyclomethicone and mixed to uniformity; and the resulting mixture added to the cyclomethicone and polysilicone-11 and mixed to uniformity. The fragrance was then added and also mixed to uniformity. The resulting fill material was degassed under vacuum, and filled into 6 minim twist-off softgel capsules, each containing 0.32 g fill material, to give a product containing 0.30% (with a 20% overage) retinol by weight of the fill material.

EXAMPLE 3
Softgel Containing Retinol, 0.15%, and Ascorbic Acid, 3%, in Silicone

A fill material for softgel capsules was prepared from the following formulation:

| Ingredient | Weight percent |
| --- | --- |
| Cyclomethicone and polysilicone-11 | 53.0 |
| Cyclomethicone | 40.2 |
| Ascorbic acid-impregnated microparticles [Preparation 2] | 6.0 |
| Retinol-impregnated microparticles [Preparation 1] | 0.8 |

The fill material was prepared and filled into softgel capsules as described in Example 1, except that both the retinol-impregnated microspheres and the ascorbic-acid impregnated microspheres were dispersed in the cyclomethicone, to give a product containing 3% ascorbic acid and 0.15% retinol (20% overage) by weight of the fill material.

EXAMPLE 4
Softgel Containing Retinol, 0.15%, in Emulsion

A fill material for softgel capsules is prepared from the following formulation:

| Ingredient | Weight percent |
| --- | --- |
| Gycereth-7 triacetate (Pelemol G7A) | 20.53 |
| Cyclomethicone (Dow Corning 245 fluid) | 18.00 |
| PEG-20 (PEG 1000) | 15.00 |
| PEG-8 (PEG 400) | 12.00 |
| Cyclomethicone and dimethicone copolyol (Dow Corning 3225C) | 11.50 |
| Glycerin | 5.00 |
| Purified water | 4.35 |
| Tribehenin (Syncrowax HRC) | 3.00 |
| Cyclomethicone and dimethiconol (Dow Corning 1401 fluid) | 2.50 |
| Polysorbate 20 (Tween 20) | 2.00 |
| Aluminum starch octenylsuccinate (Dryflo PC) | 2.00 |
| Phenyltrimethicone (Dow Corning 556 fluid) | 1.70 |
| Retinol-impregnated microparticles [Preparation 1] | 0.80 |
| Benzyl alcohol | 0.50 |
| Tocopheryl acetate | 0.50 |
| Isopropylparaben/isobutylparaben/butylparaben (Liquipar Oil) | 0.30 |
| Bisabolol | 0.10 |
| Disodium EDTA | 0.10 |
| BHT | 0.10 |
| Citric acid | 0.02 |

The process is carried out under nitrogen and yellow light. The PEG-20, PEG-8, and glycerin are heated to 65° C. and mixed to uniformity (phase 1A). The water, disodium EDTA, and citric acid are heated to 45° C. while continuously mixing until all components are dissolved (phase 1B), and phase 1B added to phase 1A with mixing and heating to 65° C. The gycereth-7 triacetate, polysorbate 20, and benzyl alcohol are heated to 65° C. and mixed to uniformity (phase 1C), and phase 1C added to phase 1A/B with mixing. The cyclomethicone and dimethicone copolyol, tribehenin, cyclomethicone and dimethiconol, phenyl trimethicone, and BHT are heated to 65° C. and mixed to uniformity (phase 2A). The cyclomethicone, tocopheryl acetate, isopropylparaben/isobutylparaben/butylparaben, and bisabolol are heated to 65° C. and mixed (phase 2B), and phase 2B added to phase 2A with mixing to uniformity. The phase 1A/1B/1C is added to phase 2A/2B with turbulent mixing to form a coarse emulsion, and the aluminum starch octenylsuccinate added and mixed. The emulsion is then cooled to 35° C. The emulsion is then homogenized, adding the retinol-impregnated microparticles. The resulting fill material is degassed under vacuum, and filled into 6 minim twist-off capsules as in Example 1.

EXAMPLE 5
Softgel Containing Retinol, 0.15%, and Ascorbic Acid, 1% Free, in Emulsion A fill material for softgel capsules is prepared from the following formulation:

| Ingredient | Weight percent |
| --- | --- |
| Gycereth-7 triacetate | 19.53 |
| Cyclomethicone | 18.00 |
| PBG-20 | 15.00 |
| PEG-8 | 12.00 |
| Cyclomethicone and dimethicone copolyol | 11.50 |
| Glycerol | 5.00 |
| Purified water | 4.35 |
| Tribehenin | 3.00 |
| Cyclomethicone and dimethiconol | 2.50 |
| Polysorbate 20 | 2.00 |
| Aluminum starch octenylsuccinate | 2.00 |
| Phenyltrimethicone | 1.70 |
| Ascorbic acid | 1.00 |
| Retinol-impregnated microparticles [Preparation 1] | 0.80 |
| Benzyl alcohol | 0.50 |
| Tocopheryl acetate | 0.50 |
| Isopropylparaben/isobutylparaben/butylparaben | 0.30 |
| Bisabolol | 0.10 |
| Disodium BDTA | 0.10 |
| BHT | 0.10 |
| Citric acid | 0.02 |

The various ingredients are mixed as in Example 3, except that the ascorbic acid is added to phase 1A; and the resulting fill material is degassed under vacuum, and filled into 6 minim twist-off capsules as in Example 1.

EXAMPLE 6
Softgel Containing Retinol, 0.15%, and Ascorbic Acid, 1% Free/1% Impregnated, in Emulsion A fill material for softgel capsules is prepared from the following formulation:

| Ingredient | Weight percent |
| --- | --- |
| Gycereth-7 triacetate | 19.18 |
| Cyclomethicone | 18.00 |
| PEG-20 | 15.00 |
| PBG-8 | 12.00 |
| Cyclomethicone and dimethicone copolyol | 11.50 |
| Glycerol | 5.00 |
| Purified Water | 4.35 |
| Tribehenin | 3.00 |
| Cyclomethicone and dimethiconol | 2.50 |
| Polysorbate-20 | 2.00 |
| Ascorbic acid-impregnated microparticles [Preparation 2] | 2.00 |
| Phenyltrimethicone | 1.70 |
| Ascorbic acid | 1.00 |

-continued

| Ingredient | Weight percent |
| --- | --- |
| Retinol-impregnated microparticles [Preparation 1] | 0.80 |
| Benzyl alcohol | 0.50 |
| Tocopheryl acetate | 0.50 |
| Isopropylparaben/isobutylparaben/butylparaben | 0.30 |
| Fragrance | 0.25 |
| Sodium metabisulfite | 0.10 |
| Bisabolol | 0.10 |
| Disodium EDTA | 0.10 |
| BHT | 0.10 |
| Citric acid | 0.02 |

The various ingredients are mixed as in Example 3, except that the additional ascorbic acid is added to phase 1A and the ascorbic acid-impregnated microparticles are added with the retinol-impregnated microparticles; and the resulting fill material is degassed under vacuum, and filled into 6 minim twist-off capsules as in Example 1.

While this invention has been described in conjunction with specific embodiments and examples, it will be evident to one of ordinary skill in the art, having regard to this disclosure, that equivalents of the specifically disclosed materials and techniques will also be applicable to this invention; and such equivalents are intended to be included within the following claims.

What is claimed is:

1. A softgel formulation containing retinol, comprising:
   (a) a soft gelatin shell; and
   (b) a fill material within the shell, the fill material comprising:
      (i) an optionally thickened silicone oil,
      (ii) retinol-impregnated microparticles.

2. The formulation of claim 1, comprising:
   (a) a soft gelatin shell; and
   (b) a fill material within the shell, the fill material comprising:
      (i) an optionally thickened silicone oil,
      (ii) retinol-impregnated microparticles in such quantity and having a retinol content such that the retinol content of the fill material is from 0.005% to 5% by weight.

3. The formulation of claim 1 containing retinol and ascorbic acid, comprising:
   (a) a soft gelatin shell; and
   (b) a fill material within the shell, the fill material comprising:
      (i) an optionally thickened silicone oil,
      (ii) retinol-impregnated microparticles, and
      (iii) ascorbic acid-impregnated microparticles.

4. The formulation of claim 3, comprising:
   (a) a soft gelatin shell; and
   (b) a fill material within the shell, the fill material comprising:
      (i) an optionally thickened silicone oil,
      (ii) retinol-impregnated microparticles in such quantity and having a retinol content such that the retinol content of the fill material is from 0.005% to 5% by weight, and
      (iii) ascorbic acid-impregnated microparticles in such quantity and having an ascorbic acid content such that the ascorbic acid content of the fill material is from 0.01% to 10% by weight.

5. The formulation of claim 1 where the optionally thickened silicone oil comprises dimethicone, cyclomethicone, or a mixture thereof.

6. The formulation of claim 1 where the optionally thickened silicone oil comprises cyclomethicone and a high molecular weight polydimethylsiloxane, polysilicone-11, a cyclomethicone and dimethicone cross-polymer, or a mixture thereof.

7. The formulation of claim 1 where the microparticles have a weight average diameter less than 50 μm.

8. The formulation of claim 7 where the microparticles have a weight average diameter of 20 μm.

9. The formulation of claim 1 where the crosslinked polymer of the microparticles is a styrene/divinylbenzene copolymer, a vinyl stearate/divinylbenzene copolymer, a methyl methacrylate/ethylene glycol dimethacrylate copolymer, or a lauryl methacrylate/ethylene glycol dimethacrylate copolymer.

10. The formulation of claim 1 where the fill material further comprises at least one additional component selected from an antioxidant, a chelating agent, a colorant, a fragrance, and a preservative.

11. The formulation of claim 2 where the retinol content of the fill material is from 0.02% to 1% by weight.

12. The formulation of claim 4 where the ascorbic acid content of the fill material is from 0.3% to 3% by weight.

13. A softgel formulation containing retinol, comprising:
    (a) a soft gelatin shell; and
    (b) a fill material within the shell, the fill material comprising:
       (i) an emulsion comprising a polyethylene glycol and a silicone oil, and
       (ii) retinol-impregnated microparticles.

14. The formulation of claim 13, comprising:
    (a) a soft gelatin shell; and
    (b) a fill material within the shell, the fill material comprising:
       (i) an emulsion comprising a polyethylene glycol and a silicone oil, and
       (ii) retinol-impregnated microparticles in such quantity and having a retinol content such that the retinol content of the fill material is from 0.005% to 5% by weight.

15. The formulation of claim 13, comprising:
    (a) a soft gelatin shell; and
    (b) a fill material within the shell, the fill material comprising:
       (i) an emulsion comprising a polyethylene glycol and a silicone oil, and
       (ii) retinol-impregnated microparticles, and
       (iii) ascorbic acid-impregnated microparticles.

16. The formulation of claim 15, comprising:
    (a) a soft gelatin shell; and
    (b) a fill material within the shell, the fill material comprising:
       (i) an emulsion comprising a polyethylene glycol and a silicone oil, and
       (ii) retinol-impregnated microparticles in such quantity and having a retinol content such that the retinol content of the fill material is from 0.005% to 5% by weight, and
       (iii) ascorbic acid-impregnated microparticles in such quantity and having an ascorbic acid content such that the ascorbic acid content of the fill material present in the ascorbic acid-impregnated microparticles is from 0.01% to 10% by weight.

17. The formulation of claim 13 where the microparticles have a weight average diameter less than 50 μm.

18. The formulation of claim 17 where the microparticles have a weight average diameter of 20 μm.

19. The formulation of claim 13 where the crosslinked polymer of the microparticles is a styrene/divinylbenzene copolymer, a vinyl stearate/divinylbenzene copolymer, a methyl methacrylate/ethylene glycol dimethacrylate copolymer, or a lauryl methacrylate/ethylene glycol dimethacrylate copolymer.

20. The formulation of claim 13 where the fill material further comprises at least one additional component selected from an antioxidant, a chelating agent, a colorant, a fragrance, and a preservative.

21. The formulation of claim 13 where the emulsion comprises up to 10% of water by weight of the emulsion.

22. The formulation of claim 14 where the retinol content of the fill material is from 0.02% to 1% by weight.

23. The formulation of claim 15 where the total ascorbic acid content of the fill material is from 0.3% to 3% by weight.

24. A softgel formulation containing retinol and ascorbic acid, comprising:
   (a) a soft gelatin shell; and
   (b) a fill material within the shell, the fill material comprising:
      (i) an emulsion comprising a polyethylene glycol and a silicone oil, and ascorbic acid present in from 0.1% to 10% by weight of the fill material, and
      (ii) retinol-impregnated microparticles.

25. The formulation of claim 24, comprising:
   (a) a soft gelatin shell; and
   (b) a fill material within the shell, the fill material comprising:
      (i) an emulsion comprising a polyethylene glycol and a silicone oil, and ascorbic acid present in from 0.01% to 10% by weight of the fill material, and
      (ii) retinol-impregnated microparticles in such quantity and having a retinol content such that the retinol content of the fill material is from 0.005% to 5% by weight.

26. The formulation of claim 24, comprising:
   (a) a soft gelatin shell; and
   (b) a fill material within the shell, the fill material comprising:
      (i) an emulsion comprising a polyethylene glycol and a silicone oil, and ascorbic acid present in from 0.1% to 10% by weight of the fill material, and
      (ii) retinol-impregnated microparticles, and
      (iii) ascorbic acid-impregnated microparticles.

27. The formulation of claim 26, comprising:
   (a) a soft gelatin shell; and
   (b) a fill material within the shell, the fill material comprising:
      (i) an emulsion comprising a polyethylene glycol and a silicone oil, and ascorbic acid present in from about 0.1% to 10% by weight of the fill material, and
      (ii) retinol-impregnated microparticles in such quantity and having a retinol content such that the retinol content of the fill material is from 0.005% to 5% by weight, and
      (iii) ascorbic acid-impregnated microparticles in such quantity and having an ascorbic acid content such that the ascorbic acid content of the fill material present in the ascorbic acid-impregnated microparticles is from 0.01% to 10% by weight.

28. The formulation of claim 24 where the microparticles have a weight average diameter less than 50 $\mu$m.

29. The formulation of claim 28 where the microparticles have a weight average diameter of 20 $\mu$m.

30. The formulation of claim 24 where the crosslinked polymer of the microparticles is a styrene/divinylbenzene copolymer, a vinyl stearate/divinylbenzene copolymer, a methyl methacrylate/ethylene glycol dimethacrylate copolymer, or a lauryl methacrylate/ethylene glycol dimethacrylate copolymer.

31. The formulation of claim 24 where the fill material further comprises at least one additional component selected from an antioxidant, a chelating agent, a colorant, a fragrance, and a preservative.

32. The formulation of claim 24 where the emulsion comprises up to 10% of water by weight of the emulsion.

33. The formulation of claim 25 where the retinol content of the fill material is from 0.02% to 1% by weight.

34. The formulation of claim 26 where the total ascorbic acid content of the fill material is from 0.3% to 3% by weight.

35. The formulation of claim 34 where the ascorbic acid content of the emulsion is from 0.3% to 3% by weight of the fill material.

* * * * *